United States Patent
Kyota

(10) Patent No.: US 8,222,436 B2
(45) Date of Patent: Jul. 17, 2012

(54) OXETANE COMPOUND, ACTIVE ENERGY RAY-CURABLE COMPOSITION, ACTIVE ENERGY RAY-CURABLE INK COMPOSITION AND INKJET RECORDING METHOD

(75) Inventor: Hirokazu Kyota, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 64 days.

(21) Appl. No.: 12/868,730

(22) Filed: Aug. 26, 2010

(65) Prior Publication Data

US 2011/0052831 A1 Mar. 3, 2011

(30) Foreign Application Priority Data

Aug. 27, 2009 (JP) ................... 2009-196862
Aug. 13, 2010 (JP) ................... 2010-181389

(51) Int. Cl.
*C07D 305/02* (2006.01)
*C09D 11/10* (2006.01)

(52) U.S. Cl. ............... 549/510; 428/195.1; 427/466; 427/487

(58) Field of Classification Search ............... 549/510; 428/195.1; 427/466, 487
See application file for complete search history.

(56) References Cited

FOREIGN PATENT DOCUMENTS

| JP | 9-183927 A | 7/1997 |
| JP | 2001-181386 A | 7/2001 |
| JP | 2003-292855 A | 10/2003 |
| JP | 2005-2166 A | 1/2005 |
| JP | 2005-036022 A | 2/2005 |
| JP | 2006-045415 A | 2/2006 |

OTHER PUBLICATIONS

STN Structure Search Results (Mar. 19, 2012).*

* cited by examiner

*Primary Examiner* — David W Wu
*Assistant Examiner* — Vu A Nguyen
(74) *Attorney, Agent, or Firm* — Solaris Intellectual Property Group, PLLC

(57) ABSTRACT

The present invention provides an oxetane compound represented by the following formula (1), and a active energy ray-curable composition including the oxetane compound as a polymerizable monomer. In formula (1), $R^{11}$ to $R^{15}$ each independently represents a hydrogen atom or an alkyl group; $R^{21}$ to $R^{24}$ each independently represents a hydrogen atom, an alkyl group, an alkoxy group or a halogen atom; R represents an alkyl group including a partial structure selected from an oxirane ring, an oxetane ring or a vinyl ether and having from 3 to 10 carbon atoms, or a vinyl group; and any adjacent groups among $R^{21}$ to $R^{24}$ and R may be bonded to each other to form a ring structure (1)

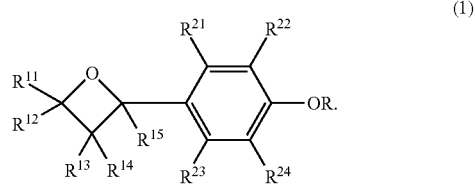

9 Claims, No Drawings

OXETANE COMPOUND, ACTIVE ENERGY RAY-CURABLE COMPOSITION, ACTIVE ENERGY RAY-CURABLE INK COMPOSITION AND INKJET RECORDING METHOD

CROSS-REFERENCE TO RELATED APPLICATION

This application claims priority under 35 USC 119 from Japanese Patent Applications No. 2009-196862 filed on Aug. 27, 2009 and No. 2010-181389 filed on Aug. 13, 2010, the disclosure of which is incorporated by reference herein.

BACKGROUND OF THE INVENTION

1. Field of the Invention

The present invention is related to a novel oxetane compound, an active energy ray-curable compound including the oxetane compound, an active energy ray-curable compound including the oxetane compound, and an inkjet recording method.

2. Description of the Related Art

Image recording methods that form an image on a recording medium such as paper based on image data signals, include electrophotographic systems, sublimation type and melt type heat transfer systems, inkjet systems and the like. The electrophotographic systems require a process of forming an electrostatic latent image on a photoreceptor drum by means of electrical charging and exposure, and thus there are problems such as complicated systems, and consequent increases in the production cost. The heat transfer systems employ inexpensive apparatuses, but since the systems make use of ink ribbons, there are problems such as high running cost and the generation of waste materials. On the other hand, the inkjet systems employ inexpensive apparatuses, and since the systems perform image formation directly on a recording medium, by jetting ink only on those image areas where necessary, an efficient use of the ink can be made at low running cost. Furthermore, the inkjet systems produce less noise, and work excellently as an image recording system.

As an inkjet ink having printing adaptability to non-absorptive recording media such as plastics, there are known ultraviolet (UV)-curable inks that cure upon irradiation with ultraviolet radiation (see, for example, Japanese Patent Application Laid-Open (JP-A) Nos. 9-183927 and 2003-292855). UV-curable inks have an advantage that the time or facilities to volatilize organic solvents are not required, as compared with solvent-based inks When such a UV-curable ink is used, systems utilizing radical polymerization of monomer components are generally used for the curing.

In recent years, ultraviolet curable inkjet inks in which a cationic polymerizable compound is used have also been proposed. However, it is not still easy to design an ink which has excellent curability and the viscosity of which is sufficiently low, whereby stable jetting is enabled. In order to address these issues, oxetane compounds having a specific structure have been proposed. That is, an inkjet ink including an oxetane compound which has a p-methoxyphenyl group at a carbon atom that is adjacent to the oxygen atom included in the oxetane ring, has been proposed (see JP-A No. 2001-181386). However, since this compound is a monofunctional compound, sufficient curability may not be attained, and the compound may be remained unreacted, which may cause safety issues. Further, a bifunctional compound of such an oxetane compound has also been reported (see, JP-A No. 2005-2166); however, since the molecular weight of such a compound is large, the viscosity may be higher and, further, when such a compound is used for an inkjet ink, jetting stability may be an issue to concern.

As such, in conventional cationic polymerizable curable compositions that are used in, for example, curable ink compositions, sufficient curing sensitivity and strength of cured film has still not been attained yet. Further, when such a conventional cationic polymerizable curable composition is used in an inkjet ink, there is a room for improvement from the viewpoint of jetting stability.

SUMMARY

The present invention has been made in view of the above circumstances and provides an novel oxetane compound represented by the following formula (1) and an active energy ray-curable composition including the oxetane compound as a polymerizable monomer.

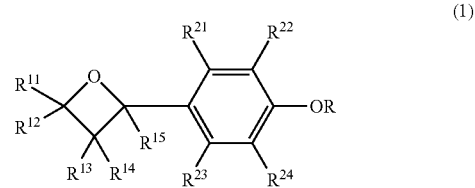

In formula (1), $R^{11}$ to $R^{15}$ each independently represents a hydrogen atom or an alkyl group; $R^{21}$ to $R^{24}$ each independently represents a hydrogen atom, an alkyl group, an alkoxy group or a halogen atom; R represents an alkyl group including a partial structure selected from an oxirane ring, an oxetane ring or a vinyl ether and having from 3 to 10 carbon atoms, or a vinyl group; and any adjacent groups among $R^{21}$ to $R^{24}$ and R may be bonded to each other to form a ring structure.

DETAILED DESCRIPTION OF THE INVENTION

Novel Oxetane Compound

The novel oxetane compound of the present invention is an oxetane compound represented by the following formula (1). Hereinafter, the oxetane compound represented by the following formula (1) may also be referred to as the "oxetane compound of the invention".

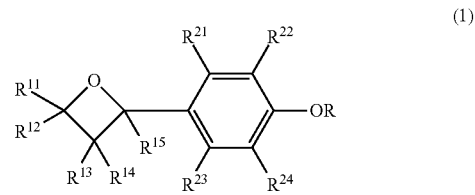

In formula (1), $R^{11}$ to $R^{15}$ each independently represents a hydrogen atom or an alkyl group. $R^{21}$ to $R^{24}$ each independently represents a hydrogen atom, an alkyl group, an alkoxy group or a halogen atom. R represents an alkyl group including a partial structure selected from an oxirane ring, an oxetane ring or a vinyl ether and having from 3 to 10 carbon atoms, or a vinyl group. Any adjacent groups among $R^{21}$ to $R^{24}$ and R may be bonded to each other to form a ring structure.

The synthesis method of the oxetane compound of the invention may be selected appropriately. The oxetane compound of the invention may be synthesized, for example, by the synthesis scheme of any of the following a) to d).

a) An example in which R is an alkyl group including an oxirane ring as a partial structure.

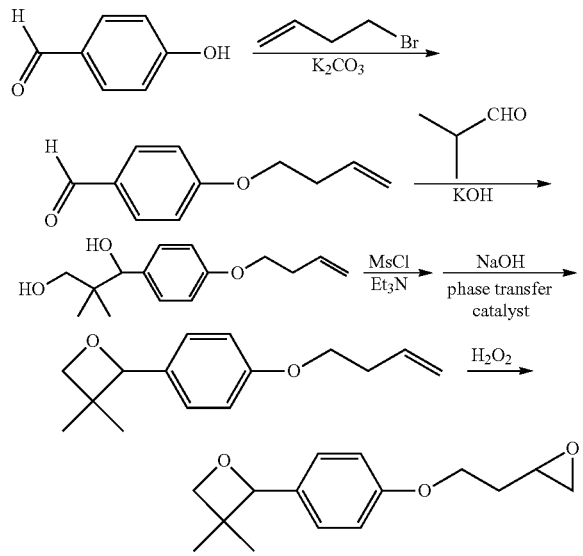

In the above synthesis scheme, the first reaction may be carried out by a general reaction of a phenol and an alkyl halide. The second to forth reactions constitute a process of forming an oxetane ring, the process including an Aldol-Cannizzaro reaction, and may be performed by the method described on page 533 of Synthesis 1995 (hereinafter, which may be referred to as Document A). In the final process, an epoxy ring is formed by an oxidation reaction, and the process may be carried out using, for example, aqueous hydrogen peroxide.

b) An example in which R is an alkyl group including an oxetane ring as a partial structure.

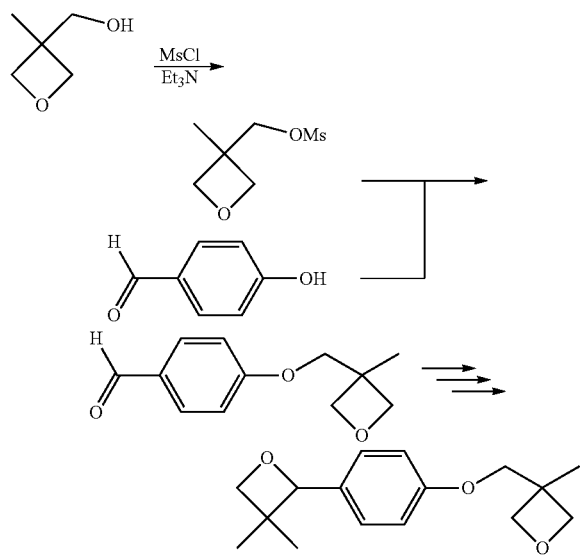

In the above scheme, the first and second reactions may be carried out as mesylation of an alcohol and alkylation of a phenol by general reactions. Thereafter, the oxetane ring may be formed by the method described in Document A.

c) An example in which R is an alkyl group including a vinyl ether as a partial structure.

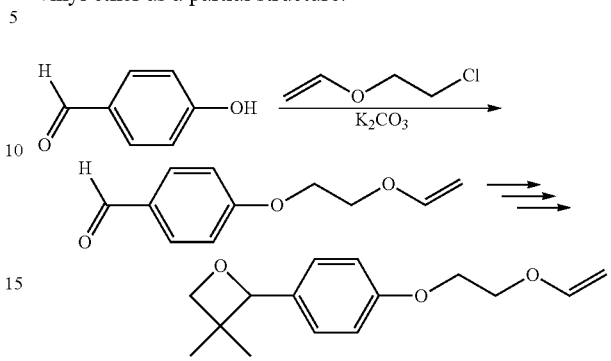

In the above scheme, the first reaction may be carried out as alkylation of a phenol by a general reaction. Thereafter, the oxetane ring may be formed by the method described in Document A.

d) An example in which R is a vinyl group

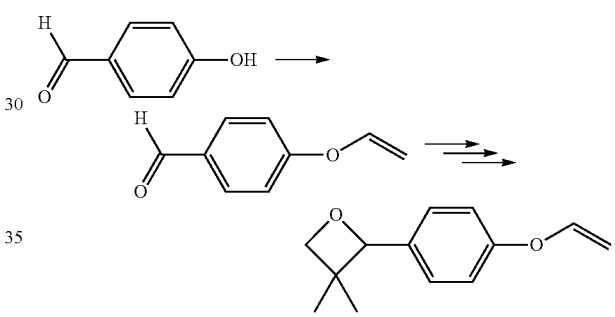

In the above scheme, the first reaction is vinyl etherification. The reaction may be carried out by, for example, a method described in J. Am. Chem. Soc. 2002, 124, 1951. The second and subsequent reactions may be carried out by the method described in Document A and the oxetane form may be formed.

Examples of the application of the oxetane compound of the invention include a polymerizable monomer, for example, used in a polymerizable composition, and a raw material for synthesis of a functional organic compound.

Examples of a polymerizable composition in which the oxetane compound of the invention may be used include active energy ray-curable compositions (for example, an ink composition). Among such active energy ray-curable composition, the oxetane compound of the invention may be preferably used in an active energy ray-curable inkjet ink composition.

Hereinbelow, exemplary embodiments of each of $R^{11}$ to $R^{15}$, $R^{21\ to\ R24}$ and R of formula (1) are described in detail.

In formula (1), $R^{11}$ to $R^{15}$ each independently represents a hydrogen atom or an alkyl group. The alkyl group represented by any of $R^{11}$ to $R^{15}$ is preferably an alkyl group having from 1 to 6 carbon atoms, and more preferably a methyl group or an ethyl group.

The alkyl group represented by any of $R^{11}$ to $R^{15}$ may further have at least one substituent, and example of the substituent include an aryl group, an alkoxy group, an aryloxy group, an alkoxycarbonyl group, and a halgen atom. The alkyl group represented by any of $R^{11}$ to $R^{15}$ is preferably an alkyl group which does not have a substituent.

More specifically, it is preferable that either one of $R^{11}$ and $R^{12}$ is a hydrogen atom or $R^{11}$ and $R^{12}$ are each a hydrogen atom. It is more preferable that $R^{11}$ and $R^{12}$ are each a hydrogen atom.

It is preferable that $R^{13}$ and $R^{14}$ are each a methyl group, or either one of $R^{13}$ and $R^{14}$ is hydrogen and the other is a methyl group. It is more preferable that $R^{13}$ and $R^{14}$ are each a methyl group.

$R^{15}$ is preferably an ethyl group, a methyl group or a hydrogen atom. $R^{15}$ is more preferably a hydrogen atom.

It is still more preferable that $R^{11}$ to $R^{15}$ are each a hydrogen atom.

In formula (1), $R^{21}$ to $R^{24}$ each independently represents a hydrogen atom, an alkyl group, an alkoxy group, or a hydrogen atom, and preferably a hydrogen atom or an alkoxy group.

The alkyl group represented by any of $R^{21}$ to $R^{24}$ is preferably an alkyl group having from 1 to 6 carbon atoms, and more preferably a methyl group or an ethyl group.

The alkyl group represented by any of $R^{21}$ to $R^{24}$ preferably has at least one substituent, and the examples of the substituent include an aryl group, an alkoxy group, an aryloxy group, an alkoxycarbonyl group, a halogen atom, and a hydroxyl group. Each of $R^{21}$ to $R^{24}$ is preferably an alkyl group which does not have a substituent.

The alkoxy group represented by any of $R^{21}$ to $R^{24}$ is preferably an alkoxy group having from 1 to 6 carbon atoms, and more preferably a methoxy group or an ethoxy group.

The alkoxy group represented by any of $R^{21}$ to $R^{24}$ may further have at least one substituent, and examples of the substituent include the substituents which the alkyl group represented by any of $R^{21}$ to $R^{24}$ may have. The alkoxy group represented by any of $R^{21}$ to $R^{24}$ is preferably an alkoxy group which does not have a substituent.

It is preferable that $R^{21}$ to $R^{24}$ are each a hydrogen atom; or three of $R^{21}$ to $R^{24}$ are a hydrogen atom and one of $R^{21}$ to $R^{24}$ is an alkoxy group; or two of $R^{21}$ to $R^{24}$ are a hydrogen atom and two of $R^{21}$ to $R^{24}$ are an alkoxy group. It is more preferable that $R^{21}$ to $R^{24}$ are each a hydrogen atom, or three of $R^{21}$ to $R^{24}$ are a hydrogen atom and one of $R^{21}$ to $R^{24}$ is an alkoxy group (still more preferably a methoxy group).

In formula (1), R represents an alkyl group including a partial structure selected from an oxirane ring (three-membered cyclic ether), an oxetane ring (four-membered cyclic ether) or a vinyl ether and having from 3 to 10 carbon atoms, or a vinyl group.

The alkyl group represented by R preferably has from 3 to 10 carbon atoms, and more preferably from 3 to 8 carbon atoms. The alkyl group represented by R may be a straight chain alkyl group or may be an alkyl group including a cyclic structure.

In the alkyl group represented by R, including an oxyrane ring or an oxetane ring as a partial structure means that together with an oxygen atom, one or more carbon atoms included in the alkyl group form an oxirane ring or an oxetane ring.

When R contains an oxirane ring as a partial structure, examples of R includes an alkyl group of terminal alkyl epoxy type, an alkyl group of glycidyl ether type and an alicyclic epoxide. R is preferably in the form of alicyclic epoxyde.

In the alkyl group represented by R, including a vinyl ether as a partial structure means that the alkyl group is an alkyl group having a vinyl ether at a terminal.

When the oxetane compound of the present invention is used as a polymerizable monomer, the oxirane ring, oxetane ring or vinyl ether included in R functions as a cationic polymerizable functional group.

The alkyl group represented by R preferably contains an oxirane ring as a partial structure, from the viewpoint of curability.

R may have at least one substituent as long as the total number of carbon atoms is from 3 to 10. The substituent is preferably an alkyl group or an alkoxy group, from the viewpoints of curability when the oxetane compound of the invention is used as a polimerizable monomer in a curable composition, and jetting stability when the oxetane compound of the invention is used in an inkjet ink composition.

Any adjacent groups among $R^{21}$ to $R^{24}$ and R may be bonded to each other to form a ring structure. The formed ring is preferably a five-membered ring or a six-membered ring. The elements that form the skeleton of the ring structure are preferably carbon atoms only or carbon and oxygen atoms.

When R and $R^{22}$ form a ring structure, the total number of carbon atoms included in R and $R^{22}$ is form 3 to 10. When R and $R^{24}$ form a ring structure, the total number of carbon atoms included in R and $R^{24}$ is form 3 to 10.

The molecular weight of the oxetane compound of the invention is preferably from 175 to 600, and more preferably from 200 to 500.

The oxetane compound of the invention may be a liquid or a solid at ordinary temperature (25° C.). When the oxetane compound is used as a polymerizable monomer, it is preferably a liquid at ordinary temperature (25° C.). When the oxetane compound is a solid and is used as a polymerizable monomer, the oxetane compound may be, for example, dissolved in another polymerizable compound and then used.

Specific examples of the oxetane compound of the invention include the following compounds. However, the oxetane compound of the invention is not limited to the following specific examples.

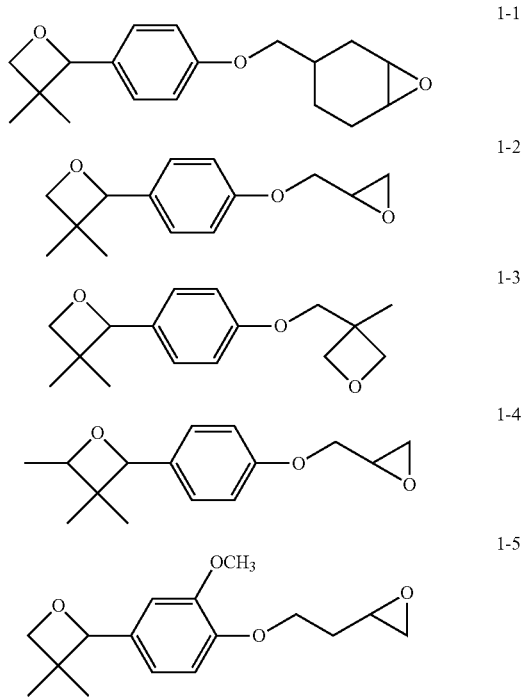

-continued

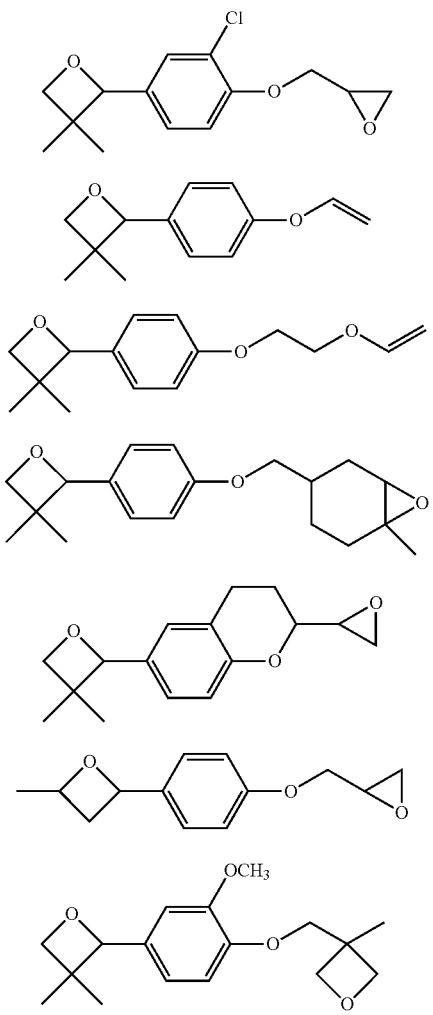

1-6
1-7
1-8
1-9
1-10
1-11
1-12

[Active Energy Ray-Curable Composition, Active Energy Ray-Curable Ink Composition]

The active energy ray-curable composition of the invention includes the oxetane compound of the invention as a polymerizable monomer. The active energy ray-curable composition of the invention may include other components as necessary.

The active energy ray-curable ink composition of the invention is an ink composition that includes the active energy ray-curable composition of the invention.

Here, the term "active energy rays" as used in the invention is not particularly limited as long as irradiation with the energy rays may provide an energy that is configured to generate an initiator species in a composition, and broadly includes α-rays, γ-rays, X-rays, ultraviolet radiation, visible radiation, electron beams and the like. Among these, ultraviolet radiation and electron beams are preferred, and particularly ultraviolet radiation is preferred, from the viewpoint of curing sensitivity and easy availability of the apparatus.

The active energy ray-curable composition of the invention includes the oxetane compound of the invention, and as a result the active energy ray-curable composition has high sensitivity to active energy ray irradiation, excellent curability, and may form a cured product which has excellent strength.

The active energy ray-curable ink composition of the invention has high sensitivity to active energy ray irradiation, and may form an image which has excellent curability. The active energy ray-curable ink composition of the invention may be used as an inkjet ink composition which has excellent jetting stability.

The active energy ray-curable composition of the invention exhibits excellent curability, especially under high humidity conditions (25° C. and 60 to 70% RH). The mechanism thereof is unclear; however, it is thought that the oxetane compound of the invention may contribute to, especially, an increase in reaction speed at the initial period of the curing reaction, and as a result, even if the composition is cured under high humidity conditions, the composition may exhibit excellent curability without being affected by (or being less affected by) polymerization inhibition.

The active energy ray-curable ink composition of the invention is an embodiment of the active energy ray-curable composition of the invention. A cured ink image may be formed by supplying the ink composition to a recording medium, and irradiating the ink composition with active energy rays. The active energy ray-curable ink composition of the invention may be preferably used as an ink composition for inkjet recording.

Hereinafter, the various constituent elements of the active energy ray-curable composition of the invention will be explained in detail, together with an active energy ray-curable ink composition as a suitable application embodiment.

In the following descriptions, the active energy ray-curable composition and active energy ray-curable ink composition of the invention will be appropriately referred to as "curable composition" and "ink composition," respectively.

(Polymerizable Compound)

The polymerizable composition of the invention and the ink composition of the invention include the oxetane compound as a polymerizable monomer.

<Oxetane Compound>

The oxetane compound of the invention, which is included as a polymerizable monomer in the polymerizable composition or ink composition of the invention, is an oxetane compound represented by formula (1) as described above and the details thereof are described in the above.

In the polymerizable composition of the invention and the ink composition of the invention, one kind of the oxetane compound of the invention may be used or two or more kinds thereof may be used in combination.

The content of the oxetane compound of the present invention is preferably from 4% by mass to 50% by mass, and more preferably from 10% by mass to 30% by mass, relative to the total mass of the polymerizable compound included in the curable composition or the ink composition. When the content is within the above ranges, the curability may be improved and, when the oxetane compound is used in an inkjet ink composition, jetting stability may also be improved. Further, when the content is within the above range, the polymerizable composition and the ink composition may also have excellent storage stability.

<Other Polymerizable Compound>

In the curable composition or the ink composition of the invention, it is preferable to use another cationic polymerizable monomer in combination, in addition to the oxetane compound of the invention.

The other cationic polymerizable monomer is not particularly limited as long as it is a compound which initiates a polymerization reaction and cures under the action of the acid generated by the compound configured to generate an acid upon irradiation with active energy rays as will be described later, and various known cationic polymerizable compounds that are known as photocationic polymerizable compounds may be used.

Examples of the other cationic polymerizable monomer include the epoxy compounds, vinyl ether compounds, oxetane compounds, and the like that are described in JP-A Nos. 6-9714, 2001-31892, 2001-40068, 2001-55507, 2001-310938, 2001-310937, 2001-220526 and the like.

In the curable composition or the ink composition of the invention, it is preferable that a polymerizable monomer including an oxirane ring, a polymerizable monomer including an oxetane ring, and/or a polymerizable monomer including vinyl ether are included in a content ratio described in detail below.

When the curable composition or the ink composition of the invention includes a polymerizable monomer including vinyl ether, the content ratio (mass ratio) is preferably 50% by mass or less, more preferably 20% by mass or less, with respect to the total mass of the polymerizable monomers included in the composition, from the viewpoint of attaining both curability and suppression of influence from the surrounding environment, such as odor.

When the curable composition or the ink composition of the invention includes a polymerizable monomer including an oxetane ring (A) and a polymerizable monomer including an oxirane ring (B), the content ratio (mass ratio) expressed as A:B (polymerizable monomer including an oxetane ring: polymerizable monomer including an oxirane ring) is preferably from 20:80 to 80:20, and more preferably, from 30:70 to 70:30, from the viewpoint of curability.

Here, in the scope of each of the polymerizable monomer including an oxirane ring, the polymerizable monomer including an oxetane ring, the polymerizable monomer including vinyl ether, both the oxetane compound of the invention and the other cationic polymerizable monomers may be included. Further, the content ratio thereof is a ratio calculated as a mass ratio with respect to the total mass of the polymerizable monomers included in the curable composition or the ink composition.

When the polymerizable monomer is a multifunctional compound including different polymerizable functional groups in the molecule thereof, the mass of the monomer is divided in accordance with the number of functional groups, and the thus obtained mass is used as the basis of the calculation of the content ratio. For example, when the compound includes one oxetane ring and one oxirane ring in the molecule thereof, and the mass of the compound is 100 g, the content ratio is calculated as 50 g of a compound including an oxetane ring and a content ratio of 50 g of a compound including an oxirane ring.

(Polymerization Initiator)

The curable composition and ink composition of the invention may contain a polymerization initiator.

The polymerization initiator may be appropriately selected for use from a photocationic polymerization initiator, a photodecolorant such as a dye, a photochromic agent, and a compound configured to generate an acid upon irradiation with the light used in microresists or the like (ultraviolet radiation having a wavelength of 400 to 200 nm, far-ultraviolet radiation, particularly preferably, g-rays, h-rays, i-rays, or KrF excimer laser light), ArF excimer laser light, electron beams, X-rays, molecular beams, ion beams or the like.

As previously mentioned, irradiation with ultraviolet radiation is suitable in the curable composition and ink composition of the invention, and therefore it is preferable to select a polymerization initiator having sensitiveness to ultraviolet radiation.

Examples of such a photocationic polymerization initiator include compound configured to generate an acid upon irradiation with active energy ray by decomposition. Examples include onium salt compounds such as a diazonium salt, a phosphonium salt, a sulfonium salt and an iodonium salt; sulfonate compounds such as imidosulfonate, oximesulfonate, diazodisulfone, disulfone and o-nitrobenzyl sulfonate; and the like.

In regard to the type of the photocationic polymerization initiator that may be used in the invention, specific compounds and preferred examples thereof, the compounds described in paragraphs (0066) to (0122) of JP-A No. 2008-13646 may be exemplified.

The polymerization initiator may be used singly or in combination of two or more compounds.

The content of the polymerization initiator in the curable composition (also including the case of applying the initiator to an ink composition) is preferably from 0.1 to 20% by mass, more preferably from 0.5 to 10% by mass, and even more preferably from 1 to 7% by mass, in terms of the solids content.

(Sensitizer)

The curable composition of the invention, and the ink composition to which the curable composition is applied, may be further added with a sensitizer that accelerates polymerization and curing.

It is preferable to use an anthracene compound as the sensitizer. The anthracene compound may be substituted with a substituent.

When the anthracene compound has a substituent, examples of the substituent include an alkyl group, an alkoxy group, an aryloxy group and the like, and among them, an alkoxy group having 1 to 4 carbon atoms is particularly preferred. In addition, the number of substituents for the anthracene is preferably 1 to 4, and more preferably 1 to 2. Particularly, the position of the substituent in the case of monosubstitution is preferably the 9-position, and the position of the substituent in the case of bisubstitution is preferably the 9-position and the 10-position. Even among these, the sensitizer is particularly preferably a 9,10-substituted anthracene compound, which is an example of bisubstitution at the 9-position and the 10-position.

The content of the anthracene compound mentioned above is preferably from 35 to 200% by mass, more preferably from 50 to 170% by mass, and even more preferably from 70 to 150% by mass relative to the total weight of the polymerization initiator. It is preferable that the preferable content of the polymerization initiator previously mentioned and the preferable content of the anthracene compound be simultaneously set to the respective ranges.

In the invention, another sensitizer other than the anthracene compound may also be added. The other sensitizer may be used singly, or in combination with the anthracene compound. The sensitizer other than the anthracene compound may be a compound that belongs to the compound family listed below and has an absorption wavelength in the wavelength region of 350 nm to 450 nm.

Examples of the other sensitizer include polynuclear aromatics (for example, pyrene, perylene, triphenylene, 2-ethyl-9,10-dimethoxyanthracene and the like), xanthenes (for example, fluorescein, eosin, erythrosine, rhodamine B, Rose Bengal and the like), cyanines (for example, thiacarbocyanine, oxacarbocyanine and the like), merocyanines (for example, merocyanine, carbomerocyanine and the like), thiazines (for example, thionine, methylene blue, toluidine blue and the like), acridines (for example, acridine orange, chloroflavin, acriflavin and the like), anthraquinones (for example, anthraquinones and the like), squaryliums (for example, squarylium and the like), coumarins (for example, 7-diethylamino-4-methylcoumarin and the like), and the like.

The content of the sensitizer in the curable composition or the ink composition of the invention is preferably from 0.01 to 20% by mass, more preferably from 0.1 to 15% by mass, and even more preferably from 0.5 to 10% by mass, relative to the total mass of the curable composition from the viewpoint of suppressing coloration of the curable composition.

Since coloration of the curable composition poses an important problem when the curable composition is used in an ink composition, it is preferable to set the content of the sensitizer to the range given above even in the case of using this curable composition in an ink composition.

(Colorant)

The curable composition and the ink composition of the invention may contain a colorant according to the purpose.

The ink composition of the invention may be made into an ink composition capable of forming visible images, by adding a colorant. Now, the colorant will be explained below, with an example of the case of an ink composition, which is a suitable application embodiment of the curable composition of the invention.

The colorant which may be used in the invention is not particularly limited, and various known coloring materials (pigments and dyes) may be appropriately selected and used in accordance with the application. For example, when it is intended to form an image having excellent weather resistance using the ink composition, a pigment is preferred. As for dyes, water-soluble dyes and oil-soluble dyes may all be used, but oil-soluble dyes are preferred.

<Pigment>

First, pigments which may be preferably used as a colorant in the curable composition and the ink composition of the invention will be described. When a pigment is used as the colorant, the colored image formed using the ink composition acquires excellent light fastness.

The pigment is not particularly limited, and generally, use may be made of all those commercially available organic pigments and inorganic pigments, pigments dispersed in insoluble resins as dispersion media, pigments having resins grafted to the pigment surface, and the like. Furthermore, resin particles dyed with a dye, and the like may also be used.

Examples of these pigments include the pigments described in Seishiro Ito, ed., "Dictionary of Pigments" (published in 2000), W. Herbst and K. Hunger, "Industrial Organic Pigments," JP-A Nos. 2002-12607, 2002-188025, 2003-26978 and 2003-342503.

Specific examples of the organic pigments and inorganic pigments that may be used in the invention include the compounds described in paragraphs (0126) to (0131) of JP-A No. 2008-13646, and these compounds are also applicable to the present invention.

Dispersion of the pigment may be carried out using dispersing apparatuses such as, for example, a ball mill, a sand mill, an attriter, a roll mill, a jet mill, a homogenizer, a paint shaker, a kneader, an agitator, a Henschel mixer, a colloid mill, an ultrasonic homogenizer, a pearl mill, and a wet jet mill.

Upon conducting dispersing of the pigment, a dispersant may be added to the composition. Examples of the dispersant include a hydroxyl group-containing carboxylic acid ester, a salt of a long-chain polyaminoamide and a high molecular weight acid ester, a salt of a high molecular weight polycarboxylic acid, a high molecular weight unsaturated acid ester, a macromolecular copolymer, a modified polyacrylate, an aliphatic polyvalent carboxylic acid, a naphthalenesulfonic acid-formalin condensate, a polyoxyethylene alkyl phosphate ester, a pigment derivative, and the like. It is also preferable to use commercially available macromolecular dispersants such as the SOLSPERSE series (trade name) manufactured by Lubrizol Corp.

Furthermore, synergists that are available in accordance with various pigments may also be used as auxiliary dispersants. These dispersants and auxiliary dispersants are preferably added in an amount of 1 to 50 parts by weight, relative to 100 parts by weight of the pigment.

In the curable composition and the ink composition, a solvent may be added as a dispersion medium for various components such as pigment, or a polymerizable compound, which is a low molecular weight component, may be used as the dispersion medium in a solventless state. However, since the ink composition of the invention is an active energy ray-curable type ink, and since the ink is cured after being applied onto a recording medium, it is preferable that the ink composition be solventless. This is because, when the solvent remains behind in a cured ink image, solvent resistance may be deteriorated or there occurs a problem of VOC (Volatile Organic Compound) concerning the remaining solvent. From this point of view, it is preferable to use a polymerizable compound as the dispersion medium, and to select a cationic polymerizable monomer having the lowest viscosity among others, from the viewpoint of enhancing the dispersion adaptability or the handlability of the ink composition.

The volume average particle size of the pigment particles in the curable composition or the ink composition is preferably from 0.02 µm to 0.60 µm, and more preferably from 0.02 µm to 0.10 µm. The maximum particle size is preferably 3 µm or less, and more preferably 1 µm or less, and the selection of pigment, dispersant and dispersion medium, the conditions for dispersing and the conditions for filtering are established to adjust the particle size to the range. As a result of this management of particle size, clogging of head nozzles may be suppressed, and storage stability of the ink, ink transparency and curing sensitivity may be maintained.

<Dye>

Next, dyes which may be preferably used as a colorant will be described.

The dye may be appropriately selected from the conventionally known compounds (dyes) and used. Specific examples include the compounds described in paragraphs (0023) to (0089) of JP-A No. 2002-114930 and paragraphs (0136) to (0140) of JP-A No. 2008-13646; and the like, and these are also applicable to the invention.

The colorant is added to the curable composition or the ink composition in an amount of preferably 0.05 to 20% by mass, and more preferably 0.2 to 10% by mass, relative to the total mass of the composition. When an oil-soluble dye is used as the colorant, it is particularly preferable to use the dye in an amount of 0.2 to 6% by mass, relative to the total mass of the composition (including the solvent).

(Ultraviolet Absorbent)

The curable composition and ink composition of the invention may be added with an ultraviolet absorbent, from the viewpoint of enhancing the weather resistance of the obtainable cured product or image, and preventing discoloration.

Examples of the ultraviolet absorbent include the benzotriazole-based compounds described in JP-A Nos. 58-185677, 61-190537, 2-782, 5-197075, 9-34057 and the like; the benzophenone-based compounds described in JP-A Nos. 46-2784 and 5-194483, U.S. Pat. No. 3,214,463, and the like; the cinnamic acid-based compounds described in JP-B Nos. 48-30492 and 56-21141, JP-A No. 10-88106, and the like; the triazine-based compounds described in JP-A Nos. 4-298503, 8-53427, 8-239368, 10-182621, Japanese Patent Application National Publication (Laid-Open) No. 8-501291, and the like; the compounds described in Research Disclosure No. 24239; and compounds which absorb ultraviolet radiation and emit fluorescence, as represented by stilbene-based and benzoxazole-based compounds, that is, so-called fluorescent whitening agents.

The amount of addition of the ultraviolet absorbent may be appropriately selected according to the purpose, but in general, the amount is about from 0.01 to 10% by mass relative to the total amount (total mass) of the curable composition or ink composition.

(Antioxidant)

The curable composition and ink composition of the invention may be added with an antioxidant, for the purpose of stability enhancement. Examples of the antioxidant include the agents described in European Patent Application Nos. 223739, 309401, 309402, 310551, 310552 and 459416; German Patent No. 3435443; JP-A Nos. 54-48535, 62-262047, 63-113536, 63-163351, 2-262654, 2-71262, 3-121449, 5-61166 and 5-119449; U.S. Pat. Nos. 4,814,262 and 4,980,275; and the like.

The amount of addition of the antioxidant may be appropriately selected according to the purpose, but in general, the amount is about from 0.01 to 10% by mass relative to the total amount (total mass) of the curable composition or ink composition.

(Discoloration Preventing Agent)

When the curable composition of the invention is used in an ink composition, use may be made of various organic and metal complex-based discoloration preventing agents. Examples of the organic discoloration preventing agents include hydroquinones, alkoxyphenols, dialkoxyphenols, phenols, anilines, amines, indanes, chromanes, alkoxyanilines, heterocycles and the like. Examples of the metal complex-based discoloration preventing agents include nickel complexes, zinc complexes and the like, and specific examples that may be used include the compounds described in Research Disclosure No. 17643 under items VII-I and VII-J; No. 15162; No. 18716, p. 650, left column; No. 36544, p. 527; No. 307105, p. 872; and the patent documents cited in No. 15162, or the compounds included in the general formula and compound examples of the representative compounds described in JP-A No. 62-215272, pp. 127-137.

The amount of addition may be appropriately selected according to the purpose, but in general, the amount is about from 0.01 to 10% by mass, relative to the total amount (total mass) of the ink composition.

(Electroconductive Salts)

When the curable composition of the invention is used in an ink composition, particularly in an ink composition for inkjet recording, electroconductive salts such as potassium thiocyanate, lithium nitrate, ammonium thiocyanate and dimethylamine hydrochloride, may be added to the composition for the purpose of controlling the jetting properties.

(Solvent)

It is also effective to add a trace amount of an organic solvent to the curable composition and ink composition of the invention, in order to improve the adhesiveness between the solid surface of a recording medium or the like, and the cured product or formed image.

Examples of the solvent include ketone-based solvents such as acetone, methyl ethyl ketone and diethyl ketone; alcohol-based solvents such as methanol, ethanol, 2-propanol, 1-propanol, 1-butanol and tert-butanol; chlorine-based solvents such as chloroform and methylene chloride; aromatic solvents such as benzene and toluene; ester-based solvents such as ethyl acetate, butyl acetate and isopropyl acetate; ether-based solvents such as diethyl ether, tetrahydrofuran and dioxane; glycol ether-based solvents such as ethylene glycol monomethyl ether and ethylene glycol dimethyl ether; and the like.

In this case, an addition to the extent that deterioration of solvent resistance does not occur is effective, and the amount is preferably in the range of 0.1 to 5% by mass, and more preferably 0.1 to 3% by mass, relative to the total weight of the curable composition or ink composition.

(Macromolecular Compound)

The curable composition and the ink composition of the invention may be added with various macromolecular compounds, for the purpose of regulating the film properties. Examples of the macromolecular compounds that may be used include an acrylic polymer, a polyvinyl butyral resin, a polyurethane resin, a polyamide resin, a polyester resin, an epoxy resin, a phenol resin, a polycarbonate resin, a polyvinyl butyral resin, a polyvinyl formal resin, shellac, a vinyl-based resin, an acrylic-based resin, a rubber-based resin, waxes, other natural resins, and the like. These may be used in combination of two or more compounds, without any problem. Among these, a vinyl-based copolymer obtainable by copolymerization of acrylic-based monomers is preferred. Furthermore, a copolymer including "a carboxyl group-containing monomer," "a methacrylic acid alkyl ester" or "an acrylic acid alkyl ester" as structural units may also be preferably used for the copolymer composition of the macromolecular binding material.

(Surfactant)

It is preferable to incorporate a known surfactant into the curable composition and the ink composition of the invention. Examples of the known surfactant include those described in JP-A Nos. 62-173463 and 62-183457. Specific examples thereof include anionic surfactants such as dialkylsulfosuccinic acid salts, alkylnaphthalenesulfonic acid salts and fatty acid salts; nonionic surfactants such as polyoxyethylene alkyl ethers, polyoxyethylene alkylaryl ethers, acetylene glycols, and polyoxyethylene-polyoxypropylene block copolymers; and cationic surfactants such as alkylamine salts and quaternary ammonium salts. It is also acceptable to use an organic fluoro compound instead of a known surfactant. The organic fluoro compound is preferably hydrophobic. Examples of the organic fluoro compound include fluorine-based surfactants, oily fluorine-based compounds (for example, fluorine oil) and solid fluorine compound resins (for example, ethylene tetrafluoride resin), and also include those described in JP-B No. 57-9053 (columns 8 to 17) and JP-A No. 62-135826.

(Storage Stabilizer)

In the curable composition and the ink composition of the invention, a basic compound may be added for the purpose of improving storage stability. Examples of the basic compound include those described in any one of JP-A Nos. 2003-231217, 2004-238456, and 2008-189766.

(Other Additives)

In addition to these, the curable composition and ink composition of the invention may be incorporated with, for example, a leveling additive, a matting agent, waxes for regulating film properties, a tackifier which does not inhibit polymerization and is intended to improve the adhesiveness to the recording medium, such as a polyolefin or PET, and the like according to necessity.

Specific examples of the tackifier include the high molecular weight adhesive polymers described in JP-A No. 2001-49200, pp. 5-6 (for example, a copolymer formed from an ester of (meth)acrylic acid and an alcohol having an alkyl group having 1 to 20 carbon atoms, an ester of (meth)acrylic acid and an alicyclic alcohol having 3 to 14 carbon atoms, and an ester of (meth)acrylic acid and an aromatic alcohol having 6 to 14 carbon atoms), low molecular weight tackifying resins having polymerizable unsaturated bonds, and the like.

(Properties Preferable when Applied to Ink Composition)

It is as previously described that since the curable composition of the invention cures with high sensitivity and is excellent in the strength and flexibility of the cured product, it is preferable to apply the curable composition to an active energy ray-curable ink composition. It is particularly preferable to apply the curable composition to an inkjet ink composition that is applicable to inkjet recording methods. Hereinbelow, preferable properties will be described when the curable composition of the invention is applied to an inkjet ink composition.

When the ink composition of the invention is applied to inkjet recording, the ink viscosity at the temperature upon jetting is preferably from 5 mPa·s to 30 mPa·s, and more preferably from 7 mPa·s to 20 mPa·s, in consideration of jettability. Therefore, it is preferable to determine the viscosity by appropriately adjusting the composition ratio so as to achieve the range mentioned above.

The viscosity of the ink composition at room temperature (25 to 30° C.) is preferably from 7 mPa·s to 120 mPa·s, and more preferably 10 mPa·s to 80 mPa·s. When the viscosity at room temperature is set high, even if a porous recording medium is used, ink penetration into the recording medium may be prevented, and reduction of uncured monomer and reduction of foul odor are made possible. Furthermore, dot bleeding at the time of landing of ink droplets may be suppressed, and as a result, image quality may be improved.

The surface tension of the ink composition of the invention is preferably from 20 mN/m to 40 mN/m, and more preferably 20 mN/m to 30 mN/m. When recording is performed using the ink composition of the invention on various recording media such as polyolefin, PET, coated paper and non-coated paper, the surface tension is preferably 20 mN/m or greater from the viewpoint of bleeding and penetration, and the surface tension is preferably 30 mN/m or less from the viewpoint of wettability.

The ink composition of the invention is applied for inkjet recording. The inkjet recording system is not particularly limited, and the inkjet recording system may be, for example, any of a charge control system which jets out ink using electrostatic attractive force; a drop-on-demand system (pressure pulse system) which uses the vibration pressure of a piezoelectric element; an acoustic type inkjet system which converts an electric signal into an acoustic beam, irradiates an ink with the acoustic beam, and jets out the ink utilizing a radiation pressure; a thermal type inkjet system which forms air bubbles by heating an ink, and utilizes the pressure generated therefrom; and the like. Furthermore, the inkjet recording system also includes a system that ejects an ink having a low concentration, called a photo ink, in the form of a large number of small-volume droplets; a system that improves the image quality using plural inks that have substantially the same color but different concentrations; or a system that makes use of a colorless transparent ink.

Among the systems described above, the ink composition of the invention is suitable as an ink for inkjet recording based on the drop-on-demand system (pressure pulse system) that makes use of a piezoelectric element.

(Inkjet Recording Method)

The ink composition of the invention may be used in an inkjet recording method including (a) a process of jetting the ink composition on a recording medium using an inkjet recording apparatus (image recording process), and (b) a process of curing the ink composition by irradiating the jetted ink composition with active energy rays (image curing process).

That is, the inkjet recording method of the invention is a method including an image recording process of forming an image by inkjet recording, and an image curing process.

A specific exemplary embodiment of the inkjet recording method of the invention will be explained below, including the details of an inkjet recording apparatus that may be suitably employed in the relevant method.

System

An exemplary form of the inkjet recording system that jets out ink may be represented by a system disclosed in JP-A No. 2002-11860, but the system is not limited to this form and may adopt other forms as well.

Ink Retaining Unit

In regard to a unit that retains ink, it is preferable to fill in the ink in a known ink cartridge, or the ink retaining unit may be contained in a deformable container to form a tank, as disclosed in JP-A No. 5-16377. Furthermore, as disclosed in JP-A No. 5-16382, if the unit is equipped with a subtank, supply of ink will be more stabilized. As disclosed in JP-A No. 8-174860, a cartridge in the form of supplying ink based on the movement of a valve when the pressure in the ink supply chamber is decreased, may also be used. Suitable methods for applying a negative pressure in order to appropriately maintain the meniscus in the head in such an ink retaining unit, include a method based on the height of the ink retaining unit, that is, the hydraulic head pressure; a method based on the capillary force of a filter provided in the ink flow channel; a method of controlling the pressure using a pump or the like; a method of maintaining the ink in an ink absorber and applying a negative pressure by means of its capillary force, as disclosed in JP-A No. 50-74341; and the like.

Ink Supply Channel

Methods for supplying ink from such an ink retaining unit to a head may include a method of directly connecting the retaining unit to a head unit, or a method of connecting the retaining unit to a head unit via a flow channel such as a tube. These ink retaining units and flow channels are preferably formed from a material such as a material having satisfactory wettability with ink, or a material that has been subjected to a surface treatment.

Head

Methods of jetting ink droplets may include a method of continuously jetting ink droplets and controlling to select whether to land the droplets slantingly on a material to be recorded in accordance with the image, as disclosed in JP-A No. 5-104725; or a method of jetting ink droplets only to those necessary portions in an image, so called as an on-demand system. The on-demand system may be a system of jetting the ink by generating an ink pressure through deformation of a structure using a piezoelectric element or the like, as disclosed in JP-A No. 5-16349, or may be a system of jetting the ink under a pressure that is generated by expansion as a result of vaporization due to thermal energy, as disclosed in JP-A No. 1-234255. Furthermore, as disclosed in JP-A No. 2001-277466, the system may also be a system of controlling the jetting to a material to be recorded under the action of an electric field.

In regard to the inkjet recording method, image recording is performed on a recording medium using the ink composition of the invention. The ink jetting nozzle used at that time or the like is not particularly limited, and may be appropriately selected according to the purpose. A nozzle in the form such as described in, for example, JP-A No. 5-31908 is applicable. In this case, when nozzles are configured in plural rows as described in JP-A No. 2002-316420 in order to jet out inks of plural colors, color images may be formed at high speed. Furthermore, if plural head units each having plural nozzle rows are arranged, a further increase in the speed may be achieved.

When nozzles are arranged at a width interval equal to or greater than the width of the image, to thereby form a so-called line head, and a material to be recorded is moved concurrently with the droplet jetted from these nozzles, as described in JP-A No. 63-160849, formation of images at high speed is made possible.

If a surface treatment such as that disclosed in JP-A No. 5-116327 is applied to the surfaces of nozzles, adhesion of airborne ink droplets to the nozzle surfaces and adhesion of ink droplets may be prevented.

Even if such a treatment is applied, dirt may still adhere in some cases, and for this reason, it is preferable to perform cleaning using a blade as disclosed in JP-A No. 6-71904.

It may not be true that inks of various colors are always equally jetted from the nozzles, and in some cases, some particular inks may not be jetted out for a long time. In such an instance, in order to maintain the meniscus stable, it is preferable to maintain the ink properties at adequate values by appropriately jetting the ink to areas outside the image area, and replenishing new ink to the head.

Even if such measures are taken, air bubbles may penetrate into the head or may be generated in the head. In this case, as described in JP-A No. 11-334092, if ink is forcibly sucked in from the outside of the head, ink with changed properties may be discarded, and at the same time, the air bubbles may be discharged out of the head. Furthermore, if ink droplet jetting is not intended for a long time, the nozzle surface may be protected by covering the nozzle surface with a cap, as described in JP-A No. 11-138830. In some cases, jetting may still not occur even if these measures are taken.

If an image is printed while some of the nozzles are incapable of jetting, there arises a problem that unevenness occurs in the image. In order to avoid such situation, it is effective to detect any nozzle that is incapable of jetting, and to take measures, as disclosed in JP-A No. 2000-343686.

When overlapped droplet jetting is carried out by mechanically moving the head unit, and synchronously moving the material to be recorded intermittently in a perpendicular direction as described in JP-A No. 6-115099, it is effective in making hardly visible of the unevenness resulting from accuracy defect in the intermittent movement of the material to be recorded, and high image quality may be realized. In this case, the relationship between image quality and the recording speed may be established into a preferable relationship, by appropriately balancing the relationship between the speed of head movement, the extent of movement of the material to be recorded, and the number of nozzles.

Furthermore, on the contrary, when the head is fixed, and the material to be recorded is mechanically made to move in a shuttling manner in a predetermined direction and at the same time, is made to move intermittently in a direction perpendicular to the predetermined direction, a similar effect may be obtained.

Temperature Control

It is preferable that the inkjet recording apparatus be equipped with a unit that stabilizes the temperature of the ink composition, and the region of the apparatus to be maintained at a constant temperature includes all members in the piping system covering from the ink tank (including an intermediate tank, if present) to the jetting surface of nozzle.

In regard to the inkjet recording method, it is preferable to heat the ink composition to 40° C. to 80° C. to decrease the viscosity of the ink composition down to 30 mPa·s or less, and preferably 20 mPa·s or less, and then to perform jetting. High jetting stability may be realized by using this method. In general, since radiation-curable ink compositions commonly have higher viscosities than those of aqueous inks, the range of fluctuation in the viscosity due to the fluctuation in temperature at the time of printing is large. Since this viscosity fluctuation of the ink composition directly exerts a large influence on the size of liquid droplets and the rate of liquid droplet jetting, and thereby causes deterioration in the image quality, it is required to maintain the temperature of the ink composition at the time of printing as constant as possible. Therefore, it is preferable to provide the inkjet recording apparatus with an ink temperature detecting unit, an ink heating unit, and a control unit that controls heating in accordance with the detected ink temperature.

The method of controlling the temperature is not particularly limited, but it is preferable to control heating in accordance with the flow rate of the ink composition and the temperature of the environment, for example, by providing plural temperature sensors at various piping sites. Furthermore, the head unit to be heated is preferably thermally shielded or insulated, so that the apparatus body is not under the influence of the temperature of air in the outside. In order to shorten the warm-up time for the printer that is required in heating, or to reduce a loss in thermal energy, it is preferable to carry out insulation from other sites, and also to decrease the overall heat capacity of the heating unit.

Alternatively, it is also suitable to have a unit that controls the energy applied to the unit for jetting ink in accordance with the ink temperature.

The control range of the ink composition temperature is preferably adjusted to the set temperature ±5° C., more preferably to the set temperature ±2° C., and even more preferably to the set temperature ±1° C.

Exposure

In regard to the light source, as described previously, a commonly used mercury lamp, metal halide lamp or the like may be used, and a light emitting diode, a semiconductor laser, a fluorescent lamp and the like may be used. Light sources, electromagnetic waves and the like, which induce the polymerization reaction of the ink, such as a hot cathode tube, a cold cathode tube, an electron beam and X-rays, may also be used.

When a metal halide lamp is used, a lamp having an output power of 10 W/cm to 1000 W/cm is used, and a metal halide lamp having an illuminance of 1 mW/cm$^2$ to 100 W/cm$^2$ at the surface of a recording medium is preferred.

When a high pressure mercury lamp, a metal halide lamp or the like is used, it is preferable to provide the inkjet recording apparatus with an exhaust unit, because ozone is generated along with electric discharge. It is suitable to have the exhaust unit disposed such that the unit also combines the function of recovering ink mist that is generated at the time of jetting of ink.

Next, preferable conditions for the irradiation with active energy rays will be described. The basic method of irradiation is disclosed in JP-A No. 60-132767. Specifically, light sources are provided on both sides of the head unit, and the head and the light source are scanned in a shuttling manner. Irradiation is carried out after the landing of the ink, after taking some time. Furthermore, curing is completed by a separate light source that does not necessitate driving. WO 99/54415 discloses a method of using an optical fiber, or a method of irradiating a recorded area with UV light by making a collimated light source incident to a mirror surface that is provided at a lateral side of the head unit, as the method of irradiation. These irradiation methods may be sufficiently used in this invention.

When an ink jetting nozzle is irradiated with an active energy ray for curing, the ink mist or the like adhering to the nozzle surface is solidified, and may pose an obstacle to ink jetting. Thus, it is preferable to take measures such as light shielding, in order to minimize irradiation of nozzles. Specifically, it is suitable to provide a barrier that prevents irradiation of the nozzle plate, or to provide a unit for limiting the incident angle to the material to be recorded so as to reduce stray light.

According to the invention, it is preferable to adjust the time taken from droplet landing to irradiation to be from 0.01 seconds to 0.5 seconds, and it is preferable to irradiate the ink composition with a radiation after from 0.01 seconds to 0.3 seconds, and more preferably from 0.01 seconds to 0.15 seconds. As such, when the time taken from droplet landing to irradiation is controlled to be extremely short, preventing the landed ink droplets from bleeding before curing may be achieved. Also, even for a porous recording medium, since the medium can be exposed before the ink composition penetrates down to the core part where the light source does not reach, unreacted monomers are inhibited from remaining behind, and consequently, an odor originating therefrom may be reduced. When the inkjet recording method described above and the ink composition of the invention are used in combination, a great synergistic effect may be obtained. When such a recording method is adopted, the dot diameter of landed ink droplets may be maintained constant even on various recording media that differ in the surface wettability, and thus the image quality is enhanced.

System Parameters

Upon forming an image, the ink landing diameter on a material to be recorded is suitably between 10 and 500 μm, and for this reason, the diameter of ink droplets at the time of jetting is preferably from 5 to 250 μm, while the nozzle diameter is preferably from 15 to 100 μm.

Upon the formation of an image, the number of pixels per inch is preferably from 50 to 2400 dpi, and therefore, the nozzle density in the head is preferably from 10 to 2400 dpi. Here, even if the nozzle density in the head is low, when the nozzles are tilted against the direction of conveyance of the material to be recorded, or when plural head units are arranged to be relatively tilted, landing at a high density may be realized using a head with large nozzle intervals. Furthermore, high density image recording may be realized by conveying the material to be recorded to a predetermined extent whenever the head moves at a low nozzle pitch as a result of the shuttling movement of the head or material to be recorded as described above, and thus landing ink droplets at different positions.

The amount of ink droplet jetting to a recording medium may be suitably controlled to be any amount between 0.05 g/m$^2$ and 25 g/m$^2$, so as to express a satisfactory gradation, and it is preferable to control the size of the ink droplets jetted from the head, and/or the quantity thereof, in order to realize this amount.

In regard to the distance between the head and the material to be recorded, if the distance is too broad, air flows out concomitantly with the movement of the head or the material to be recorded, and the flight of the ink droplets is disrupted, so that the accuracy on the position of landing is decreased. On the other hand, if the distance is too narrow, there is a risk that the head and the material to be recorded are brought to contact because of the surface unevenness of the material to be recorded, vibration caused by the conveyance mechanism, or the like. Thus, the distance is preferably maintained at about 0.5 mm to 2 mm.

Ink Set

The ink may be of a single color, or may be of cyan, magenta and yellow colors. The ink may be a set of four colors including black, or inks of specific colors other than these colors, which are called special colors, may also be used. The coloring material may be a dye or a pigment. In regard to the order of droplet jetting of these inks, the droplet jetting may be carried out such that the inks are made to land in an order of increasing brightness, or may be carried out such that the inks are made to land in an order of decreasing brightness. Thus, it is preferable to carry out the droplet jetting in a suitable order in terms of the image recording quality.

If the inks are superimposed in order from a color of the highest brightness, it is easy for the active energy ray to reach to the ink in the lower part, while inhibition of the curing sensitivity, an increase in the residual monomers, generation of foul odor, and deterioration of adhesiveness hardly occur. In regard to the irradiation, all of the colors may be jetted and collectively exposed, but it is preferable from the viewpoint of curing acceleration, to expose each color separately.

In regard to the image signals to be recorded, it is preferable to subject the signals to signal processing so as to obtain satisfactory color reproducibility, as described in JP-A No. 6-210905 for example.

The ink composition of the invention may also be used in three-dimensional modeling applications, for example, in the applications of forming a printing ink receiving section in a planographic printing plate as previously mentioned, in addition to the inkjet recording applications, and the ink composition may also be used for canister printing applications or food product applications. In these applications, images may be formed using known methods, and reference may be made to, for example, the descriptions of Japanese Patent No. 2679586 and the like.

<Recording Medium>

As for the recording medium on which recording is performed using the ink composition of the invention, ink-permeable recording media and non-ink-permeable recording media may be used together. Examples of the ink-permeable recording media include ordinary papers, papers exclusive for inkjet use, coated papers, papers for general and electrophotographic use, fabrics, unwoven fabrics, porous films, macromolecular absorbers, and the like. These are described as "materials to be recorded" in JP-A No. 2001-1891549 and the like.

Example of the non-ink-permeable recording media include art papers, synthetic resins, rubbers, resin-coated papers, glass, metals, porcelain, wood, and the like. In addition, use may also be made of base materials prepared by combining a number of these materials and processing into complex materials to add the respective functions.

Any synthetic resin may be used as the synthetic resin used as a non-ink-permeable recording medium, but for example, polyesters such as polyethylene terephthalate and polybutadiene terephthalate; polyolefins such as polyvinyl chloride, polystyrene, polyethylene, polyurethane and polypropylene; and acrylic resins, polycarbonates, acrylonitrile-butadiene-styrene copolymers, diacetates, triacetates, polyimides, cellophane, celluloids, and the like may be mentioned.

The shape (thickness) of a recording medium utilizing a synthetic resin may have a film shape, a card shape or a block shape, and may be appropriately selected according to the desired purpose without particularly limitation. These synthetic resins may be transparent or may be opaque. In regard to the form of use of the recording medium utilizing a synthetic resin, the synthetic resin may be used in the form of the film that is used in so-called soft packaging according to a preferred embodiment, and various non-absorptive plastics and films thereof may be used. Examples of the films formed from various plastics include polyethylene terephthalate (PET) films, biaxially stretched polystyrene (OPS) films, biaxially stretched polypropylene (OPP) films, biaxially stretched nylon (ONy) films, polyvinyl chloride (PVC) films, polyethylene (PE) films, and triacetylcellulose (TAC) films.

Examples of the resin-coated paper used as a non-ink-permeable recording medium, include transparent polyester films, opaque polyester films, opaque polyolefin resin films, and paper supports laminated on both surfaces with polyolefin resins. The paper supports laminated on both surfaces with polyolefin resins are particularly preferred.

EXAMPLES

Hereinafter, the present invention will be described by way of Examples, but the invention is not intended to be limited to these Examples. In the present Example, an instance of preparing an ink for inkjet recording will be shown as an example of the ink composition. Unless particularly stated otherwise, "parts" are on a mass basis.

Synthesis Example 1

Oxetane compound (1-1) that is an oxetane compound of the invention was synthesized by the following scheme.

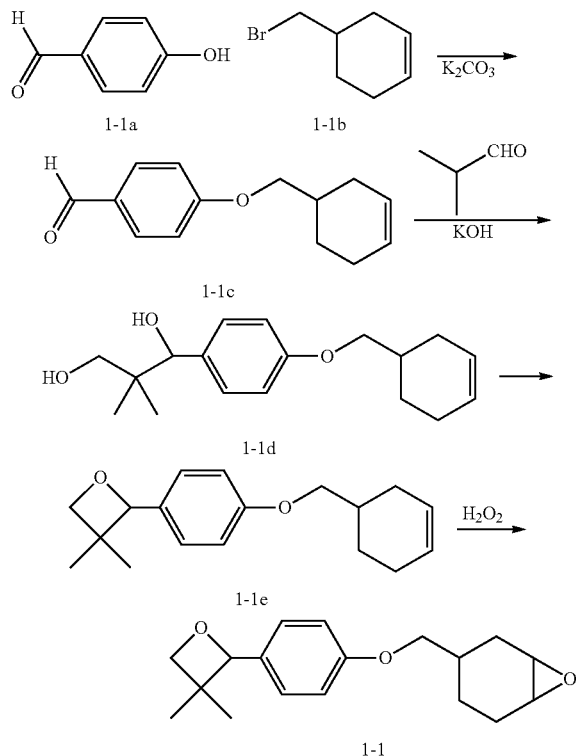

<Synthesis of Intermediate Product (1-1c)>

To 2.0 L of N,N-dimethylacetamide solution containing 61 g (0.5 mol) of p-hydroxybenzaldehyde (manufactured by Tokyo Chemical Industry, Co., Ltd.), 87.5 g (0.5 mol) of compound (1-1b) (which was synthesized by the method described in Tetrahedron 1989, 45, 363) and 276 g (2.0 mol) of potassium carbonate (manufactured by Wako Pure Chemicals Industries, Ltd.) were added, while the solution was being stirred. The obtained mixture was heated at a temperature of 100° C. for 6 hours. Thereafter, ethyl acetate and water were added to the mixture for phase separation. The organic layer was washed with water, 0.5N sulfuric acid, and 1 wt % aqueous sodium hydroxide solution, and washed with saturated saline solution twice, followed by drying with anhydrous sodium sulfate. Then the solvent was distilled away under reduced pressure and 101 g of intermediate product (1-1c) was obtained. The thus obtained 101 g of intermediate product (1-1c) was used in the next reaction.

<Synthesis of Intermediate Product (1-1d)>

101 g of the crude product of intermediate product (1-1c) and 170 g (1.0 mol) of isobutyl aldehyde (manufactured by Wako Pure Chemicals Industries, Ltd.) were dissolved in 1.2 L of methanol. To this mixture, 500 mL of 2N aqueous potassium hydroxide solution was added dropwise, while the temperature in the container was maintained at 40° C. or lower. The reaction liquid was refluxed for three hours and, thereafter, 0.6 L of the solvent was distilled away under reduced pressure. To this liquid, ethyl acetate and water were added for phase separation, and the organic layer was washed with water and saturated saline solution each twice, followed by drying with anhydrous sodium sulfate. After the solvent was distilled away, purification was performed by silica gel chromatography. Accordingly, 67 g of intermediate product (1-1d) was obtained (0.23 mol, yield of 46% for 2 steps).

<Synthesis of Oxetane Compound (1-1)>

200 mL of dichloromethane solution containing 58 g (0.20 mol) of intermediate product (1-1d) and 24.2 g (0.20 mol) of triethylamine was cooled to a temperature of 0° C. To this solution, 25.2 g (0.22 mol) of methane sulfonyl chloride (manufactured by Wako Pure Chemicals Industries, Ltd.) was added in 5 divided additions, while the solution was being stirred. After the reaction liquid was stirred for 2 hours at room temperature, water was added to the liquid for phase separation, and the aqueous layer was removed. To the organic layer, 1.5 g of tetrabutylammonium hydrogensulfate (manufactured by Wako Pure Chemicals Industries, Ltd.) and 100 mL of 50% sodium hydroxide were added, and the thus obtained mixture was stirred for 4 hours at room temperature. Water was added to the mixture for phase separation, and the organic layer was washed with water once, and washed with saturated saline solution twice, thereby obtaining a crude product of compound (1-1e). Then, to a dicloromethane solution of the thus obtained crude product of compound (1-1e), 130 mg of methyltrioxorhenium (manufactured by Sigma-Aldrich), and 2.3 g of 3-methylpyrazole (manufactured by Tokyo Chemical Industry, Co., Ltd.) were added, while the solution was being stirred. The temperature in the container was cooled to 15° C. using water-cooling, and 25.5 mL of 31% aqueous hydrogen peroxide was added dropwise to this solution, while the temperature in the container was maintained within a range of from 15° C. to 35° C. After the completion of the dropwise addition, reflux was performed for two hours under heating using an oil bath, followed by cooling to 5° C. by ice-cooling. Then, 65 g of 10% aqueous sodium sulfite solution was added dropwise thereto. Then the organic phase was washed with saturated saline solution twice, and dried with anhydrous sodium sulfate, followed by distilling away the solvent. Then, purification using silica gel chromatography was performed, thereby 21.9 g of oxetane compound (1-1) was obtained (yield of 38% from intermediate product (1-1d)).

The data of ¹H-NMR of the oxetane compound (1-1) was shown as follows.

Oxetane compound (1-1): ¹H NMR (CDCl₃, 300 MHz), δ: 0.80 (s, 3H), 1.39 (s, 3H), 2.3 (m,2H), 2.6 (m, 1H), 2.9 (m, 1H), 3.1 (m, 1H), 4.15 (t, 2H), 4.23 (d, 1H), 4.57 (d, 1H), 5.49 (s, 1H), 6.92 (d, 2H), 7.23 (d, 2H)

Synthesis 2

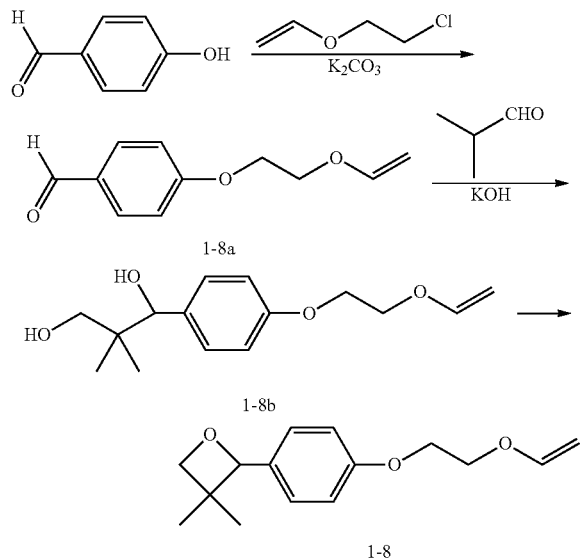

<Synthesis of Intermediate Product (1-8a)>

To 2.0 L of N,N-dimethylacetamide solution containing 61 g (0.5 mol) of p-hydroxybenzaldehyde (manufactured by Tokyo Chemical Industry, Co., Ltd.), 51.3 g (0.5 mol) of 2-chloroethylvinyl ether (manufactured by Wako Pure Chemicals Industries, Ltd.) and 276 g (2.0 mol) of potassium carbonate (manufactured by Wako Pure Chemicals Industries, Ltd.) were added, while the solution was being stirred. The obtained mixture was heated at a temperature of 140° C. for 6 hours. Thereafter, ethyl acetate and water were added to the mixture for phase separation. The organic layer was washed with water, 0.5N sulfuric acid, and 1 wt % aqueous sodium hydroxide solution, and washed with saturated saline solution twice, followed by drying with anhydrous sodium sulfate. Then the solvent was distilled away under reduced pressure and 72 g of an intermediate product (1-8a) was obtained. The thus obtained 72 g of intermediate product (1-8a) was used in the next reaction.

<Synthesis of Intermediate Product (1-8b)>

82 g of the crude product of intermediate product (1-8a) and 170 g (1.0 mol) of isobutyl aldehyde (manufactured by Wako Pure Chemicals Industries, Ltd.) were dissolved in 1.2 L of methanol. To this mixture, 500 mL of 2N aqueous potassium hydroxide solution was added dropwise, while the temperature in the container was maintained at 40° C. or lower. The reaction liquid was refluxed for three hours and, thereafter, 0.6 L of the solvent was distilled away under reduced pressure. To this liquid, ethyl acetate and water were added for phase separation, and the organic layer was washed with water and saturated saline solution each twice, followed by drying with anhydrous sodium sulfate. After the solvent was distilled away, purification was performed by silica gel chromatography. Accordingly, 51 g of intermediate product (1-8b) was obtained (0.19 mol, yield of 38% for 2 steps).

<Synthesis of Oxetane Compound (1-8)>

200 mL of dichloromethane solution containing 51 g (0.19 mol) of intermediate product (1-8b) and 24.2 g (0.20 mol) of triethylamine was cooled to a temperature of 0° C. To this solution, 25.2 g (0.22 mol) of methane sulfonyl chloride (manufactured by Wako Pure Chemicals Industries, Ltd.) was added in 5 divided additions, while the solution was being stirred. After the reaction liquid was stirred for 2 hours at room temperature, water was added to the liquid for phase separation, and the aqueous layer was removed. To the organic layer, 1.5 g of tetrabutylammonium hydrogensulfate (manufactured by Wako Pure Chemicals Industries, Ltd.) and 100 mL of 50% aqueous sodium hydroxide solution were added, and the thus obtained mixture was stirred for 4 hours at room temperature. Water was added to the mixture for phase separation, and the organic layer was washed with saturated saline solution twice, and dried with anhydrous sodium sulfate, followed by distilling away the solvent. Then, purification using silica gel chromatography was performed, thereby 25.9 g of oxetane compound (1-8) was obtained (yield of 55% from intermediate product (1-8b)).

The data of ¹H-NMR of the oxetane compound (1-8) was shown as follows.

Oxetane compound (1-8): ¹H NMR (CDCl₃, 300 MHz), δ: 0.81 (s, 3H), 1.39 (s, 3H), 3.6-4.4 (m,8H), 5.55 (s, 1H), 6.5 (m, 1H), 6.9 (d, 2H), 7.2 (d, 2H)

Example 1

1. Preparation of Pigment Dispersion

25% by mass of C. I. Pigment Red (manufactured by CIBA Specialty Chemicals; trade name: CROMOPHTAL JET MAGENTA DMQ), 65% by mass of 3-ethyl-3-phenoxymethyl oxetane (manufactured by Toa Gosei Co., Ltd.; trade name: OXT-211) and 10% by mass of a dispersant (trade name: SOLSPERSE 32000; manufactured by Lubrizol) were placed in a boll mill in this composition ratio, and were dispersed for 16 hours using zirconia beads having a diameter of 0.6 mm.

2. Preparation of Magenta UV Inkjet Ink Composition

The thus obtained pigment dispersion, polymerizable monomers (oxetane compound (1-1) and other polymerizable monomers), a polymerization initiator, and a sensitizing dye were mixed so as to obtain composition 1 as described below, and the mixture was stirred using a high speed water cooling type stirrer, thereby obtaining a magenta UV inkjet ink composition.

| (Composition 1) | |
|---|---|
| Colorant: C.I. Pigment Red 122 (manufactured by CIBA Specialty Chemicals; trade name: CROMOPHTAL JET MAGENTA DMQ) | 5.0 parts |
| Dispersant: (trade name: SOLSPERSE 32000; manufactured by Lubrizol) | 2.0 parts |
| Oxetane compound (1-1) | 20.0 parts |
| Bifunctional epoxy compound: limonene dioxide (manufactured by Daicel Chemical Industries, Ltd.; trade name: CELOXIDE 3000) | 35.0 parts |
| Bifunctional oxetane compound (manufactured by Toa Gosei Co., Ltd.; trade name: OXT-221) | 24.0 parts |
| Monofunctional oxetane compound (manufactured by Toa Gosei Co., Ltd.; trade name: OXT-211) | 21.0 parts |
| Photo cationic polymerization initiator (the structure of which is shown as B-1): | 5.0 parts |

-continued (Composition 1)

(tris(4-chlorophenyl)sulfonium hexafluorophosphate)

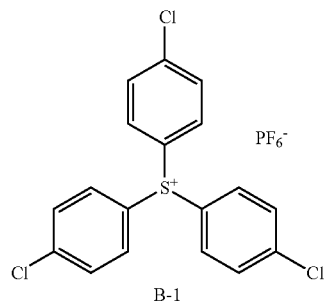

B-1

Sensitizing dye: 9,10-butoxyanthracene (manufactured by Kawaski Kasei Chemicals Ltd.)     3.0 parts Examples 2 to 11 and Comparative Examples 1 to 4

Ink compositions for of Examples 2 to 11 and Comparative Examples 1 to 4 each were prepared in substantially the same manner as the composition 1 of Example 1, except that in Examples 2 to 11 and Comparative Examples 1 to 4, the compounds and the amount thereof used in composition 1 of Example 1 were changed in accordance with the compositions of Examples 2 to 11 and Comparative Examples 1 to 4 described in Tables 1 and 2.

Further, as comparative compounds of the polymerizable monomer, compound A-1 having the structure shown below (compound described in JP-A No. 2001-181386), compound A-2 having the structure shown below (compound described in JP-A No. 2005-2166), and Compound A-3 having the structure shown below, were used.

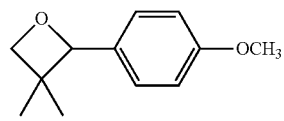

A-1

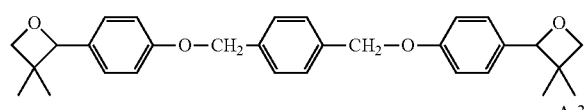

A-2

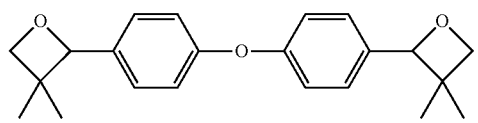

A-3

TABLE 1

| | | | Ex. 1 | Ex. 2 | Ex. 3 | Ex. 4 | Ex. 5 | Ex. 6 | Ex. 7 | Ex. 8 | Ex. 9 | Ex. 10 | Ex. 11 |
|---|---|---|---|---|---|---|---|---|---|---|---|---|---|
| Polymer-izable monomer | Oxetane Compound of the Invention | 1-1 | 20 | | | | | | 40 | 8 | 20 | 20 | |
| | | 1-2 | | 20 | | | | | | | | | |
| | | 1-3 | | | 20 | | | | | | | | |
| | | 1-4 | | | | 20 | | | | | | | |
| | | 1-5 | | | | | | | | | | | 20 |
| | | 1-6 | | | | | | 20 | | | | | |
| | | 1-8 | | | | | 20 | | | | | | |
| | Bifunctonal oxirane | CELOXIDE-3000 | 35 | 35 | 35 | 35 | 35 | 35 | 25 | 41 | 3 | 62 | 35 |
| | Bifunctional oxetane | OXT-221 | 24 | 24 | 24 | 24 | 24 | 24 | 14 | 30 | 56 | 0 | 24 |
| | Monofunctional oxetane | OXT-211 | 21 | 21 | 21 | 21 | 21 | 21 | 21 | 21 | 21 | 21 | 21 |
| Colorant | | CHROMOPHTHAL JET MAGENTA DMQ (PR-122) | 5 | 5 | 5 | 5 | 5 | 5 | 5 | 5 | 5 | 5 | 5 |
| Dispersant | | SOLSPERSE 32000 | 2 | 2 | 2 | 2 | 2 | 2 | 2 | 2 | 2 | 2 | 2 |
| Polymerization initiator | | B-1 | 5 | 5 | 5 | 5 | 5 | 5 | 5 | 5 | 5 | 5 | 5 |
| Sensitizer | | 9,10-dibutoxy-anthracene | 3 | 3 | 3 | 3 | 3 | 3 | 3 | 3 | 3 | 3 | 3 |

OXT-221 (trade name): bis(3-ethyl-3-oxetanylmethyl)ether (manufactured by Toa Gosei Co., Ltd.)
OXT-211 (trade name): 3-ethyl-3-phenoxymethyl oxetane (manufactured by Toa Gosei Co., Ltd.)
CELOXIDE-3000 (trade name): limonene dioxide (manufactured by Daicel Chemical Industries, Ltd.)
Ex: Example

TABLE 2

| | | | Comparative Example 1 | Comparative Example 2 | Comparative Example 3 | Comparative Example 4 |
|---|---|---|---|---|---|---|
| Polymer-izable monomer | Comparative compound | A-1 | 20 | | | |
| | | A-2 | | 20 | | |
| | | A-3 | | | 20 | |
| | Bifunctonal oxirane | Celoxide-3000 | 35 | 35 | 35 | 45 |
| | Bifunctional oxetane | OXT-221 | 24 | 24 | 24 | 24 |
| | Monofunctional oxetane | OXT-211 | 21 | 21 | 21 | 21 |

TABLE 2-continued

|  |  | Comparative Example 1 | Comparative Example 2 | Comparative Example 3 | Comparative Example 4 |
|---|---|---|---|---|---|
| Colorant | CHROMOPHTHAL MAGENTA JET DMQ (PR-122) | 5 | 5 | 5 | 5 |
| Dispersant | SOLSPERSE 32000 | 2 | 2 | 2 | 2 |
| Polymerization initiator | B-1 | 5 | 5 | 5 | 5 |
| Sensitizer | 9,10-dibutoxy-anthracene | 3 | 3 | 3 | 3 |

OXT-221 (trade name): bis(3-ethyl-3-oxetanylmethyl)ether (manufactured by Toa Gosei Co., Ltd.)
OXT-211 (trade name): 3-ethyl-3-phenoxymethyl oxetane (manufactured by Toa Gosei Co., Ltd.)
CELOXIDE-3000 (trade name): limonene dioxide (manufactured by Daicel Chemical Industries, Ltd.)

Using each ink composition obtained in Examples 1 to 11 and Comparative Examples 1 to 4, printing and exposure were performed as described below, and evaluation was performed regarding sensitivity and jetting stability in accordance with the following evaluation method and evaluation criteria. The results are shown in Table 3.

<Printing and Exposure>

Each of the ink compositions was used to perform droplet jetting using an inkjet head of a piezoelectric system. The head has 318 nozzles at a nozzle density of 150 per 25.4 mm, and as these nozzles are fixed in two nozzle rows, with one row shifted along the direction of the row at an interval of ½ of the nozzle interval, so that 300 droplets per 25.4 mm are jetted in the direction of nozzle arrangement on the medium.

The head and the ink are controlled such that the vicinity of the jetting section is at 50±0.5° C., by circulating warm water within the head. Ink jetting from the head is controlled by a piezoelectric driving signal applied to the head, so as to enable jetting of 6 to 42 pl per one droplet. In the present Examples and Comparative Examples, droplet jetting occurs from the head, while the medium is conveyed at a position 1 mm below the head. The speed of conveyance may be set up in the range of 50 to 200 mm/s. The piezoelectric driving frequency may be set up to 4.6 kH at maximum, and the amount of droplet jetting may be controlled based on these settings.

The amount of ink jetting was controlled to be 24 pl by setting the speed of conveyance at 90 mm/s and the driving frequency at 1.9 kHz, and thereby droplet jetting was carried out at a rate of 10 g/m². Thus, solid printed images were obtained.

The medium is conveyed to the exposure unit after being subjected to droplet jetting, and is exposed using an ultraviolet light emitting diode (UV-LED). In the present Examples and Comparative Examples, "NCCU033 (trade name)" manufactured by Nichia Corp. was used as the UV-LED. This UV-LED emits an ultraviolet light having a wavelength of 365 nm from the tip, and when an electric current of about 500 mA is passed through, a light of about 100 mW is emitted from the tip. A number of the diodes are arranged at an interval of 7 mm, and a power of 0.3 W/cm² is obtained at the medium surface. The time taken from the droplet jetting to the exposure, and the duration of exposure may be changed on the basis of the speed of conveyance of the medium, and the distance between the head and the LED in the direction of conveyance. In the present Examples and Comparative Examples, exposure is achieved about 0.5 seconds after the impact. The exposure energy on the medium may be adjusted to a value between 0.01 and 15 J/cm², in accordance with the settings for the distance to the medium and the speed of conveyance. In the present Examples and Comparative Examples, the exposure energy was adjusted on the basis of the speed of conveyance. In the measurement of these exposure power and exposure energy, use was made of a value obtained by integration over a wavelength range of 220 to 400 nm using a spectroradiometer URS-40D (trade name) manufactured by Ushio, Inc. In the present Examples and Comparative Examples, a PET film having 50 μm-thick or a polyvinyl chloride sheet was used as the medium, and the printing and exposure test was carried out in an environment at 23° C. and 60% R.H. The thickness of the cured image was 19 μm.

(1. Evaluation of Sensitivity)

Each of the ink compositions was used to perform printing on a polyvinyl chloride sheet using the apparatus described above. The amount of integral exposure was adjusted by changing the speed of conveyance, and the ink was cured, to thereby obtain a printed matter. The exposure energy used during the curing was measured with an integrating radiometer (trade name: UV POWERMAP, manufactured by EIT, Inc.). Curability was determined based on the presence or absence of surface tackiness of the printed matter, and the minimum amount of integral exposure resulting in the absence of tackiness was evaluated by the following criteria.

<Evaluation Criteria>

A: Less than 100 mJ/cm²

B: 100 mJ/cm² or greater and less than 200 mJ/cm²

C: 200 mJ/cm² or greater and less than 300 mJ/cm²

D: 300 mJ/cm² or greater and less than 500 mJ/cm²

E: 500 mJ/cm² or greater and less than 10000 mJ/cm²

F: 1000 mJ/cm² or greater

For practical purposes, the rating of sensitivity needs to be C or higher, preferably to be B, and particularly preferably to be A.

(2. Evaluation of Jetting Stability)

The ink compositions were stored for 4 weeks at room temperature, and recording was performed on a recording medium using an inkjet recording apparatus having piezoelectric type inkjet nozzles. The presence or absence of dot omission and scattering of ink were observed by the naked eye after continuous printing for 48 hours at normal temperature, and an evaluation was performed on the basis of the following criteria.

<Evaluation Criteria>

A: Dot omission or ink scattering does not occur, or occurs up to 2 times.

B: Dot omission or ink scattering occurs 3 to 10 times.

C: Dot omission or ink scattering occurs 11 times or more.

TABLE 3

| | Example 1 | Example 2 | Example 3 | Example 4 | Example 5 | Example 6 | Example 7 | Example 8 | Example 9 |
|---|---|---|---|---|---|---|---|---|---|
| Integrated exposure amount (mJ/cm$^2$) | A | B | C | C | C | C | A | C | C |
| Jetting stability | A | A | A | A | A | A | B | A | A |

| | Example 10 | Example 11 | Comparative Example 1 | Comparative Example 2 | Comparative Example 3 | Comparative Example 4 |
|---|---|---|---|---|---|---|
| Integrated exposure amount (mJ/cm$^2$) | C | B | E | B | D | E |
| Jetting stability | A | A | A | C | B | A |

As shown in the results of Table 3, the ink compositions of Examples 1 to 11, which are the ink compositions containing an oxetane compound of the invention, have both excellent sensitivity and excellent jetting stability. When comparing Examples 1 and 2 with Examples 3 and 4, it is found that among the oxetane compounds of the invention, compounds in which R in formula (1) includes an oxirane ring as a partial structure is more preferable.

All publications, patent applications, and technical standards mentioned in this specification are herein incorporated by reference to the same extent as if each individual publication, patent application, or technical standard was specifically and individually indicated to be incorporated by reference.

What is claimed is:

1. An oxetane compound represented by the following formula (1):

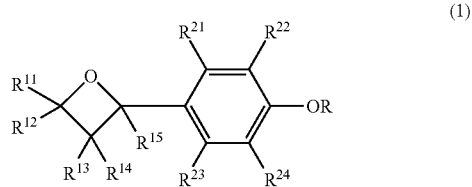

(1)

wherein, in formula (1), $R^{11}$ to $R^{15}$ each independently represents a hydrogen atom or an alkyl group; $R^{21}$ to $R^{24}$ each independently represents a hydrogen atom, an alkyl group, an alkoxy group or a halogen atom; R represents an alkyl group including a partial structure selected from an oxirane ring, an oxetane ring or a vinyl ether and having from 3 to 10 carbon atoms, or a vinyl group; and any adjacent groups among $R^{21}$ to $R^{24}$ and R may be bonded to each other to form a ring structure.

2. The oxetane compound of claim 1, wherein, in formula (1), R is an alkyl group including an oxirane ring as a partial structure and having from 3 to 10 carbon atoms.

3. The oxetane compound of claim 1, wherein, in formula (1), $R^{11}$, $R^{12}$ and $R^{15}$ are each a hydrogen atom.

4. The oxetane compound of claim 1, wherein, in formula (1), $R^{21}$ to $R^{24}$ are each a hydrogen atom; or three of $R^{21}$ to $R^{24}$ are a hydrogen atom and one of $R^{21}$ to $R^{24}$ is an alkoxy group; or two of $R^{21}$ to $R^{24}$ are a hydrogen atom and two of $R^{21}$ to $R^{24}$ are an alkoxy group.

5. An active energy ray-curable composition comprising the oxetane compound of claim 1 as a polymerizable monomer.

6. The active energy ray-curable composition of claim 5, wherein the content of the oxetane compound represented by formula (1) is from 10% by mass to 30% by mass with respect to a total mass of polymerizable monomers included in the active energy ray-curable composition.

7. An active energy ray-curable ink composition comprising the active energy ray-curable composition of claim 5.

8. The active energy ray-curable ink composition of claim 7, wherein the ink composition is an ink composition for inkjet recording.

9. An inkjet recording method comprising:
jetting the active energy ray-curable ink composition of claim 7 on to a recording medium using an inkjet recording device; and
curing the ink composition by irradiating the jetted ink composition with active radiation.

* * * * *